United States Patent [19]

Findeisen et al.

[11] Patent Number: 5,266,555
[45] Date of Patent: * Nov. 30, 1993

[54] SUBSTITUTED TRIAZOLES

[75] Inventors: Kurt Findeisen; Dietmar Kuhnt, both of Leverkusen; Klaus-Helmut Müller, Duesseldorf; Klaus König, Odenthal; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[*] Notice: The portion of the term of this patent subsequent to Jun. 4, 2008 has been disclaimed.

[21] Appl. No.: 911,450

[22] Filed: Jul. 10, 1992

[30] Foreign Application Priority Data

Jul. 20, 1991 [DE] Fed. Rep. of Germany ....... 4124150

[51] Int. Cl.$^5$ ................. A01N 43/653; C07D 249/14
[52] U.S. Cl. .................................... 504/273; 548/264.8
[58] Field of Search .......... 548/264.8; 71/92; 504/273

[56] References Cited

U.S. PATENT DOCUMENTS 5,021,081 6/1991 Findeisen et al. ............... 548/264.8

Primary Examiner—Patricia L. Morris
Attorney, Agent, or Firm—Sprung Horn Kramer & Woods

[57] ABSTRACT

The invention relates to new substituted triazoles of the general formula (1)

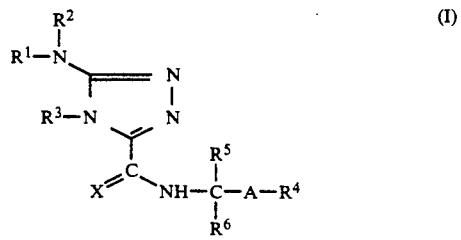

in which
$R^1$ represents alkyl,
$R^2$ represents alkyl,
$R^3$ represents alkyl,
$R^4$ represents in each case optionally substituted cycloalkyl or aryl,
$R^5$ represents either hydrogen, alkyl or cyano and
$R^6$ represents hydrogen or alkyl or
$R^5$ and $R^6$ together represent divalent alkanediyl,
A represents one of the radicals $-CH_2-CH_2-$; $-CH(CH_3)-CH_2-$; $-CH_2-O-$; $-CH_2-S-$; $-CH_2-N(R^7)-$; $-CH=CH-$ or $-C\equiv C-$ and
X represents oxygen or sulphur, where
$R^7$ represents hydrogen, alkyl or alkanoyl,
but with the exception of the compound 5-dimethylamino-4-methyl-3-(4-phenylbut-2-ylaminocarbonyl)-1,2,4-triazole,
a plurality of processes for their preparation, and their use as herbicides.

18 Claims, No Drawings

SUBSTITUTED TRIAZOLES

The invention relates to new substituted triazoles, to a plurality of processes for their preparation, and to their use as herbicides.

It has been disclosed that certain substituted triazoles such as, for example, the compound 5-dimethylamino-4-methyl-3-(4-phenylbut-2-ylaminocarbonyl)-1,2,4-triazole, have herbicidal properties (compare, for example, DE 3,809,053).

However, the herbicidal activity of these previously known compounds with respect to problem weeds as well as their tolerance by important crop plants is not entirely satisfactory in all fields of application.

There have been found new substituted triazoles of the general formula (I)

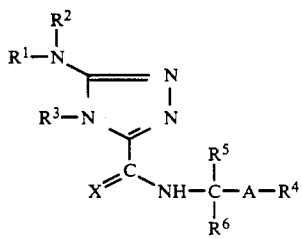

in which
$R^1$ represents alkyl,
$R^2$ represents alkyl,
$R^3$ represents alkyl,
$R^4$ represents in each case optionally substituted cycloalkyl or aryl,
$R^5$ represents either hydrogen, alkyl or cyano and
$R^6$ represents hydrogen or alkyl or
$R^5$ and $R^6$ together represent divalent alkanediyl,
A represents one of the radicals —CH$_2$—CH$_2$—; —CH(CH$_3$)—CH$_2$—; —CH$_2$—O—; —CH$_2$—S—; —CH$_2$—N(R$^7$)—; —CH=CH— or —C≡C— and
X represents oxygen or sulphur, where
$R^7$ represents hydrogen, alkyl or alkanoyl,
but with the exception of the compound 5-dimethylamino-4-methyl-3-(4-phenylbut-2-ylaminocarbonyl)-1,2,4-triazole.

The compounds of the formula (I) may exist in the form of geometric and/or optical isomers or isomer mixtures of various compositions, depending on the nature of the substituents. The invention claims pure isomers as well as isomer mixtures.

Furthermore, it has been found that the new substituted triazoles of the general formula (I)

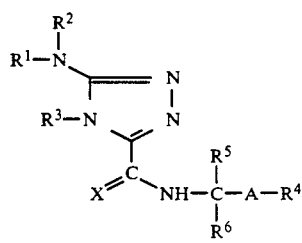

in which
$R^1$ represents alkyl,
$R^2$ represents alkyl,
$R^3$ represents alkyl,
$R^4$ represents in each case optionally substituted cycloalkyl or aryl,
$R^5$ represents either hydrogen, alkyl or cyano and
$R^6$ represents hydrogen or alkyl or
$R^5$ and $R^6$ together represent divalent alkanediyl,
A represents one of the radicals —CH$_2$—CH$_2$—; —CH(CH$_3$)—CH$_2$—; —CH$_2$—O—; CH$_2$—S—; —CH$_2$—N(R$^7$)—; —CH=CH— or —C≡C— and
X represents oxygen or sulphur, where
$R^7$ represents hydrogen, alkyl or alkanoyl,
but with the exception of the compound 5-dimethylamino-methyl-3-(4-phenylbut-2-ylaminocarbonyl)-1,2,4-triazole,
are obtained when a) aminoguanidines of the formula (II)

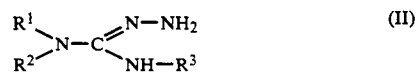

in which
$R^1$, $R^2$ and $R^3$ have the abovementioned meaning, or their acid addition salts are reacted with (thio)oxamates of the formula (III)

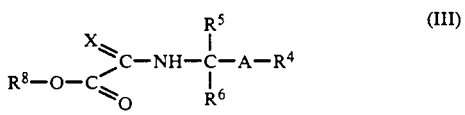

in which
$R^4$, $R^5$, $R^6$, X and A have the abovementioned meaning and
$R^8$ represents alkyl, if appropriate in the presence of a diluent and if appropriate in the presence of a reaction auxiliary, or when b) substituted triazolyl(thio)carboxylates of the formula (IV)

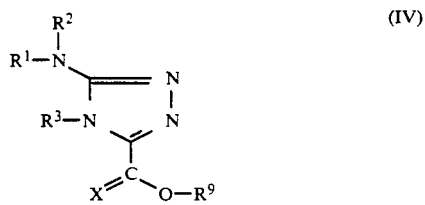

in which
$R^1$, $R^2$, $R^3$ and X have the abovementioned meaning and
$R^9$ represents alkyl, are reacted with amines of the formula (V)

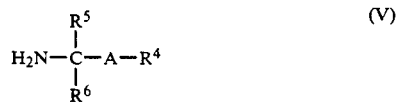

in which
$R^4$, $R^5$, $R^6$ and A have the abovementioned meaning, if appropriate in the presence of a diluent.

Finally, it has been found that the new substituted triazoles of the general formula (I) possess herbicidal properties.

Surprisingly, the substituted triazoles of the general formula (I) according to the invention show a considerably better herbicidal activity with respect to problem weeds combined with a similarly good tolerance by important crop plants compared with the substituted triazoles known from the prior art such as, for example, the compound 5-dimethylamino-4-methyl-3-(4-phenylbut-2-ylaminocarbonyl)-1,2,4-triazole, which are related compounds chemically and from the point of view of their action.

Formula (I) provides a general definition of the substituted triazoles according to the invention. Preferred compounds of the formula (I) are those in which $R^1$ represents straight-chain or branched alkyl having 1 to 6 carbon atoms, $R^2$ represents straight-chain or branched alkyl having 1 to 6 carbon atoms, $R^3$ represents straight-chain or branched alkyl having 1 to 6 carbon atoms, $R^4$ represents cycloalkyl which has 3 to 7 carbon atoms and which is optionally monosubstituted or polysubstituted by identical or different substituents, suitable substituents being: halogen, cyano, in each case straight-chain or branched alkyl having 1 to 4 carbon atoms and in each chain straight-chain or branched halogenoalkyl having in each case 1 to 4 carbon atoms and 1 to 9 identical or different halogen atoms; furthermore represents aryl which has 6 to 10 carbon atoms and which is optionally monosubstituted or polysubstituted by identical or different substituents, suitable substituents being: halogen, cyano, nitro, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, dialkylamino having in each case 1 to 4 carbon atoms in the individual straight-chain or branched alkyl moieties, N-alkanoylamino having 1 to 5 carbon atoms in the straight-chain or branched alkanoyl moiety, divalent dioxyalkylene which has 1 to 3 carbon atoms and which is optionally monosubstituted or polysubstituted by identical or different halogen substituents, and phenyl, phenoxy, α-naphthyl or β-naphthyl, each of which is optionally monosubstituted or polysubstituted by identical or different substituents from the series comprising halogen and/or straight-chain or branched alkyl having 1 to 4 carbon atoms;

$R^5$ either represents hydrogen, straight-chain or branched alkyl having 1 to 6 carbon atoms or cyano and $R^6$ represents hydrogen or straight-chain or branched alkyl having 1 to 6 carbon atoms or $R^5$ and $R^6$ together represent divalent alkanediyl having 2 to 9 carbon atoms, A represents a radical of the formula —CH$_2$—CH$_2$—; —CH(CH$_3$)—CH$_2$—; —CH$_2$—O—; —CH$_2$—S—; —CH$_2$—N(R$^7$)—; —CH=CH— or —C≡C— and X represents oxygen or sulphur, where $R^7$ represents hydrogen, straight-chain or branched alkyl having 1 to 6 carbon atoms or straight-chain or branched alkanoyl having 1 to 7 carbon atoms, but with the exception of the compound 5-dimethylamino-methyl-3-(4-phenylbut-2-ylaminocarbonyl)-1,2,4-triazole.

Particularly preferred compounds of the formula (I) are those in which $R^1$ represents straight-chain or branched alkyl having 1 to 4 carbon atoms, $R^2$ represents straight-chain or branched alkyl having 1 to 4 carbon atoms, $R^3$ represents straight-chain or branched alkyl having 1 to 4 carbon atoms, $R^4$ represents cyclopropyl, cyclobutyl, cyclopentyl or cyclohexyl, each of which is optionally monosubstituted to pentasubstituted by identical or different substituents, suitable substituents in each case being: fluorine, chlorine, bromine, cyano, methyl, ethyl, n- or i-propyl, chloromethyl, dichloromethyl, trichloromethyl, difluoromethyl or trifluoromethyl; furthermore represents phenyl, α-naphthyl, β-naphthyl or indanyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, or phenyl, phenoxy, α-naphthyl or β-naphthyl, each of which is optionally monosubstituted to trisubstituted by identical or different substituents from the series comprising fluorine, chlorine, bromine, methyl, ethyl, methoxy and/or ethoxy, $R^5$ either represents hydrogen, straight-chain or branched alkyl having 1 to 4 carbon atoms or cyano and $R^6$ represents hydrogen or straight-chain or branched alkyl having 1 to 4 carbon atoms or $R^5$ and $R^6$ together represent divalent alkanediyl having 4 to 9 carbon atoms, A represents one of the radicals —CH$_2$—CH$_2$—; —CH(CH$_3$)—CH$_2$—; —CH$_2$—O—; —CH$_2$—S—; —CH$_2$—N(R$^7$)—; —CH=CH— or —C≡C— and X represents oxygen or sulphur, where $R^7$ represents hydrogen, straight-chain or branched alkyl having 1 to 4 carbon atoms or straight-chain or branched alkanoyl having 1 to 5 carbon atoms, ps but with the exception of the compound 5-dimethylamino-4-methyl-3-(4-phenylbut-2-ylaminocarbonyl)1,2,4-triazole.

Very particularly preferred compounds of the formula (I) are those in which $R^1$ represents methyl, $R^2$ represents methyl or ethyl, $R^3$ represents methyl or ethyl, $R^4$ represents cyclohexyl which is optionally monosubstituted or disubstituted by identical or different substituents from the series comprising methyl, ethyl and/or trifluoromethyl, or represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, or phenyl, phenoxy, α-naphthyl or β-naphthyl, each of which is optionally monosubstituted to trisubstituted by identical or different substituents from the series comprising fluorine, chlorine, bromine, methyl, ethyl, methoxy and/or ethoxy, $R^5$ represents hydrogen, methyl, ethyl or cyano, $R^6$ represents methyl, ethyl, n- or i-propyl, A represents one of the radicals —CH$_2$—CH$_2$—; —CH(CH$_3$)—CH$_2$—; —CH$_2$—O—; —CH$_2$—S—; —CH$_2$—N(R$^7$)—; —CH=CH— or —C≡C— and X represents oxygen, where $R^7$ represents hydrogen, methyl, ethyl, n- or i-propyl, acetyl or propionyl, but with the exception of the compound 5-dimethylamino-4-methyl-3-(4-phenylbut-2-ylaminocarbonyl)1,2,4-triazole.

Reference is made in particular to the compounds mentioned in the Preparation Examples.

If, for example, 1-amino-2,2,3-trimethylguanidinium hydrochloride and monoethyl ethyl N-[1-(2-chlorophenyl)but-3-yl]oxamate are used as starting substances, the course of the reaction of process (a) according to the invention can be represented by the following equation:

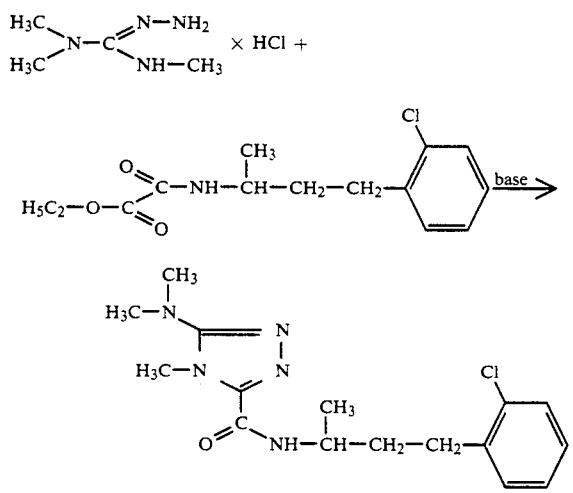

If, for example, methyl 5-dimethylamino-3-methyl-1,2,4-triazole-3-yl-carboxylate and 4-(4-methylphenyl)-but-2-ylamine are used as starting substances, the course of the reaction of process (b) according to the invention can be represented by the following equation:

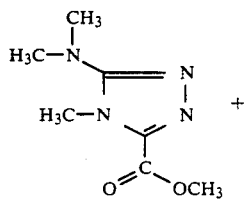

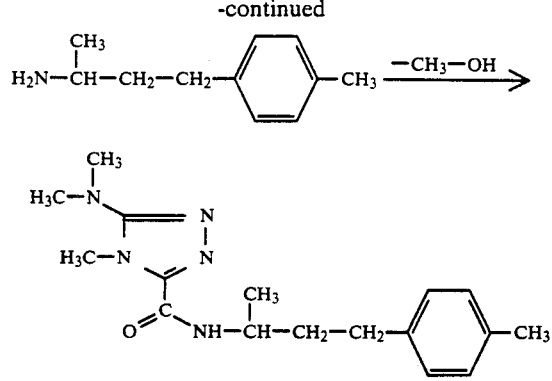

Formula (II) provides a general definition of the aminoguanidines required as starting substances for carrying out process (a) according to the invention. In this formula (II), $R^1$, $R^2$ and $R^3$ preferably represent those radicals which have already been mentioned in connection with the description of the compounds of the formula (I) according to the invention as being preferred for these substituents.

The aminoguanidines of the formula (II) and the acid addition salts thereof such as, in particular, the hydrochlorides or hydrobromides thereof, are known (compare, for example, J. Org. Chem. 19, 1807 [1954]; Bull. Soc. Chim. Fr. 1975, 1649; U.S. Pat. No. 2,845,458; DE 3,809,053).

Formula (III) provides a general definition of the (thio)oxamates furthermore required as starting substances for carrying out process (a) according to the invention. In this formula (III), $R^4$, $R^5$, $R^6$, X and A preferably represent those radicals which have already been mentioned in connection with the compounds of the formula (I) according to the invention as being preferred for these substituents. $R^8$ preferably represents straightchain or branched alkyl having 1 to 4 carbon atoms, in particular methyl or ethyl. The (thio)oxamates of the formula (III) are known or can be obtained in analogy to known processes (compare, for example, EP 273,328; Ind. J. Chem. Sect. B, 24B, 940–947 [1985]; Acta Pharm. Suec., 20, 349–364 [1983] or CA 100:174345; An. Quim. 73, 1177–1183 [1977] or CA 89:129148; Bull. Soc. Chim. Belg. 85, 421–425 [1976]; Tetrahedron Lett. 1976, 2289–2290; Bull. Chem. Soc. Jpn. 60, 609–612 [1987] or DE 3,809,053).

Formula (IV) provides a general definition of the substituted triazolyl(thio)carboxylates required as educts for carrying out process (b) according to the invention. In this formula (IV), $R^1$, $R^2$, $R^3$ and X preferably represent those radicals which have already been mentioned in connection with the description of the substances of the formula (I) according to the invention as being preferred for these substituents. $R^9$ preferably represents straightchain or branched alkyl having 1 to 4 carbon atoms, in particular methyl or ethyl.

The substituted (thio)oxamates of, the formula (IV) are known or can be obtained in analogy to known processes (compare, for example, Houben-Weyl, "Methoden der organischen Chemie [Methods in Organic Chemistry]", Volume VIII, page 659, Thieme Verlag Stuttgart; U.S. Pat. No. 2,857,390; Compt. Rend. Acad. Sci. 230, 848, [1950]; GB 1,578,719; DE 2,819,878; DE 1,227,451; DE 3,809,052).

Formula (V) provides a general definition of the amines furthermore required as educts for carrying out process (b) according to the invention. In this formula (V), $R^4$, $R^5$, $R^6$ and A preferably represent those radicals which have already been mentioned in connection with the description of the substances of the formula (I) according to the invention as being preferred for these substituents.

The amines of the formula (V) are known or can be obtained in analogy to known processes (compare, for example, EP 273,328; Ind. J. Chem. Sect. B, 24B, 940–947 [1985]; Acta Pharm. Suec., 20, 349–364 [1983] or CA 100:174345; An. Quim. 73, 1177–1183 [1977] or CA 89:129148; Bull. Soc. Chim. Belg. 85, 421–425 [1976]; Tetrahedron Lett. 1976, 2289–2290; Bull. Chem. Soc. Jpn. 60, 609–612 [1987]).

Suitable diluents for carrying out process (a) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, or alcohols such as methanol, ethanol, n- or i-propanol, n-, i-, s- or t-butanol, ethylene glycol monomethyl ether or ethylene glycol monoethyl ether.

Process (a) according to the invention is preferably carried out in the presence of a suitable reaction auxiliary. Suitable reaction auxiliaries are all customary inorganic or organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between +30° C. and +150° C., preferably at temperatures between +50° C. and +80° C.

For carrying out process (a) according to the invention, 1.0 to 1.5 moles, preferably 1.0 to 1.2 moles, of substituted (thio)oxamates of the formula (III) and, if appropriate, 1.0 to 5.0 moles, preferably 1.0 to 2.5 moles of base as a reaction auxiliary are generally employed per mole of aminoguanidine of the formula (II) or a corresponding acid addition salt. The reaction is carried out and the reaction products are worked up and isolated by known methods (in this context, compare for example DE 3,809,053 or the Preparation Examples).

Suitable diluents for carrying out process (b) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; nitriles such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate.

When carrying out process (b) according to the invention, the reaction temperatures can be varied within a substantial range. In general, the process is carried out at temperatures between +50° C. and +250° C., preferably at temperatures between +100° C. and +220° C.

Process (b) according to the invention is generally carried out under atmospheric pressure. However, it is also possible to carry out the process under increased pressure; in this case, preferred pressure ranges are between 1.0 and 50.0 bar, in particular pressure ranges between 3.0 and 20.0 bar.

For carrying out process (b) according to the invention, 1.0 to 1.5 moles, preferably 1.0 to 1.2 moles, of amine of the formula (V) are employed per mole of substituted triazolyl(thio)carboxylate of the formula (IV). The reaction is carried and the reaction products are worked up and isolated by known processes (in this context, compare for example DE 3,809,053 or the Preparation Examples).

The end products of the formula (I) are purified with the aid of customary processes, for example by column chromatography or by recrystallisation. They are characterised with the aid of the melting point or, in the case of non-crystallising compounds, with the aid of proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledon cultures of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land and for the selective combating of weeds in annual cultures.

In this context, the active compounds according to the invention can be employed with particularly good success for combating dicotyledon weeds in monocotyledon cultures such as, for example, wheat or maize.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin5(4H)-one (METRIBUZIN) for combating weeds in soya beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2,6-diethyl-N-methoxymethylacetanilide (ALACHLOR); methyl-6,6-dimethyl-2,4-dioxo-3-[1-(2-propenyloxyamino)-butylidene]-cyclohexanecarboxylic acid (ALLOXYDIM); 4-aminobenzenesulphonyl-methyl carbamate (ASULAM); 2-chloro-4-ethylamino-6-isopropylamino-1,3,5-triazine (ATRAZINE); methyl 2-[[[[(4,6-dimethoxypyrimidin-2-yl)-amino]-carbonyl]-amino]-sulphonyl]methyl)-benzoate (BENSULFURON); 3-isopropyl-2,1,3-benzothiadiazin-4-one-2,2-dioxide (BENTAZONE); methyl 5-(2,4-dichlorophenoxy)-2-nitrobenzoate (BIFENOX); 3,5-dibromo-4-hydroxy-benzonitrile; (BROMOXYNIL); N-(butoxymethyl)-2-chloro-N-(2,6-diethylphenyl)-acetamide (BUTACHLOR); N-(butoxymethyl)-2-chloro-N-(2,6-diethylphenyl)-acetamide (BUTACHLOR); 5-amino-4-chloro-2-phenyl-2,3-dihydro-3-oxy-pyridazine (CHLORIDAZON); ethyl 2-{[(4-chloro-6-methoxy-2-pyrimidinyl)-aminocarbonyl]-aminosulphonyl}-benzoate (CHLORIMURON); N-(3-chlorophenyl)isopropyl carbamate (CHLORPROPHAM); 2-chloro-N-{[(4-methoxy-6-methyl-1,3,5-triazin-2-yl)-amino]-carbonyl)benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); N,S-diethyl N-cyclohexylthiocarbamate (CYCLOATE); 2-[1-(ethoximino)-butyl]-3-hydroxy-5-(tetrahydro(2H)-thiopyran-3-yl]-2-cyclohexen-1-one (CYCLOXYDIM); 2,6-dichlorobenzonitrile (DICHLOBENIL); 2-[4-(2,4-dichlorophenoxy)-phenoxy]-propionic acid, its methyl ester or its ethyl ester (DICLOFOP); S-ethyl N,N-di-n-propylthiocarbamidate (EPTAME); 4-amino-6-t-butyl-3-ethylthiol-1,2,4-triazin-5(4H)-one (ETHIOZIN); 2-{4-[(6-chloro-2-benzoxazolyl)-oxy)-phenoxy)-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethylphenyl)-urea (FLUOMETURON); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 5-(2-chloro-4-trifluoromethyl-phenoxy)-N-methylsulphonyl-2-nitrobenzamide (FOMESAFEN); N-phosphonomethyl-glycine (GLYPHOSATE); 2-{4-[(3-chloro-5-(trifluoromethyl)-2-pyridinyl)-oxy]phenoxy}-propanoic acid or its ethyl ester (HALOXYFOP); 3-cyclohexyl-6-dimethylamino-1-methyl-1,3,5-triadine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETRABENZ); 2-(4,5-dihydro-4-methyl-4-isopropyl-5-oxo-1H-imidazol-2-yl)-pyridine-3-carboxylic acid (IMAZAPYR); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); 2-ethoxy-1-methyl-2-oxo-ethyl5- [2-chloro-4-(trifluoromethyl)-phenoxy]-2-nitrobenzoate (LACTOFEN); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)carbonyl]-amino]-sulphonyl}-benzoic acid or its methyl ester (METSULFURON); S-ethyl N,N-hexamethylene-thiocarbamate (MOLINATE); 1-(3-trifluoromethyl-phenyl)4-methylamino-5-chloro-6-pyridazone (NORFLURAZON); 4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 3-(ethoxycarbonylaminophenyl) N-(3'-methylphenyl)- carbamate (PHENMEDIPHAM); 4-amino-3,5,6-trichloropyridine-2-carboxylic acid (PICLORAM); α-chloro-2',6'-diethyl-N-(2-propoxyethyl)-acetanilide (PRETILACHLOR); 2-chloro-N-isopropylacetanilide (PROPACHLOR); isopropyl-N-phenylcarbamate (PROPHAM); O-(6-chloro-3-phenyl-pyridazin-4-yl) S-octyl thiocarbonate (PYRIDATE); ethyl 2-[4-(6-chloroquinoxalin-2-yl-oxy)-phenoxy]-propionate (QUIZALOFOPETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); S-[(4-chlorophenyl)-methyl] N,N-diethylthiocarbamate (THIOBENCARB); S-(2,3,3-trichloroallyl) N,N-diisopropylthiocarbamate (TRI-ALLATE); 2,6-dinitro-4-trifluoromethyl-N,N-dipropylaniline (TRIFLURALIN); N-(2,4-difluorophenyl-2-[3-trifluoromethylphenoxy]-3-pyridinecarboxamide (DIFLUFENICAN); N-(3,4-dichlorophenyl)-propionanilide (PROPANIL); 3,5,6-trichloro-2-pyridyloxy acetic acid (TRICLOPYR); 2-methoxy-3,6-dichlorobenzoic acid or its methyl ester (DICAMBA); 3-methoxycarbonylaminophenyl)-N-phenyl-carbamate (DESMEDIPHAM); 2-ethyl-6'-methyl-N-ethoxymethyl-2-chloroacetanilide (ACETOCHLOR); 2-ethoxy-2-oxoethyl 5-(2-chloro-4-trifluoromethylphenoxy)-2-nitrobenzoate (FLUOROGLYCOFEN); 5-(2-chloro-6-fluoro-4-trifluoromethyl-phenoxy)-N-ethylsulphonyl-2-nitrobenzamide (HALOSAFEN); 2-[1-ethoximino)propyl]-3-hydroxy-5-(2,4,6-trimethylphenyl)2-cyclohexen-1-one (TRALKOXYDIM); N-[[[[(4,6-dimethoxy-2-pyrimidinyl)amino]-carbonyl]-amino]-sulphonyl]-N-methyl-methanesulphonamide (AMIDOSULFURON); 2-(2-methoxy-ethoxy)-N[[(4,6-dimethoxy-1,3,5-triazin-2-yl)-amino]-carbonyl]-benzenesulphonamide (CINOSULFURON); 2-[[[[(4,6-dimethoxy-2-pyrimidinyl)-amino]-carbonyl]-amino]-sulphonyl]-N,N-dimethyl-3-pyridinecarboxamide (NICOSULFURON); ethyl 5-[[[[(4,6-dimethoxy-2-pyrimidinyl)-amino]-carbonyl]-amino]-sulphonyl]-1-methyl-1H-pyrazole-4-carboxylate (PYRAZOSULFURON); 3-[[[[(4-methoxy-6-methyl-1,3,5-triazin-2-yl)-amino]-carbonyl]-amino]-sulphonyl]-thiophene-2-carboxylic acid or its methyl ester (THIAMETURON, THIFENSULFURON); 2-(2-chloroethoxy-)-N-[[(4-methoxy-6-methyl-1,3,5-triazin-2-yl)-amino]-carbonyl]-benzenesulphonamide (TRIASULFURON); methyl 2-[[[[(4-methoxy-6-methyl-1,3,5-triazin-2-yl)-methylamino]-carbonyl]-amino ]-sulphonyl]-benzoate (TRIBENURON); S-(phenylmethyl) (1,2-dimethylpropyl)-ethyl-thiocarbamate (ESPROCARB); S-(phenylmethyl) dipropyl-thiocarbamate (PROSULFOCARB); 4-ethylamino-2-t-butylamino-6-chloro-1,3,5-triazine (TERBUTYLAZIN); 2,3-dihydro-3,3-dimethyl-5-benzofuranyl ethanesulphonate (BENFURESATE); 2-[(2-chlorophenyl)methyl]-4,4-dimethyl-3-isoxazolidinone (CLOMAZONE, DIMETHAZONE); S,S-dimethyl 2-difluoromethyl-4-(2-methylpropyl)-6-trifluoromethyl-3,5-pyridinedicarbothioate (DITHIOPYR); N-[3-(1-ethyl-1-methylpropyl)-isoxazol-5-yl]-2,6-dimethoxybenzamide (ISOXABEN); 3,7-dichloro-8-quinolinecarboxylic acid (QUINCHLORAC); 7-chloro-3-methyl-8-quinolinecarboxylic acid (QUINMERAC) or the trimethylsulphonium salt of N-phosphomethylglycine (SULFOSATE) may be advantageous.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per ha.

The preparation and use of the active compounds according to the invention can be seen from the following examples.

PREPARATION EXAMPLES

Example 1

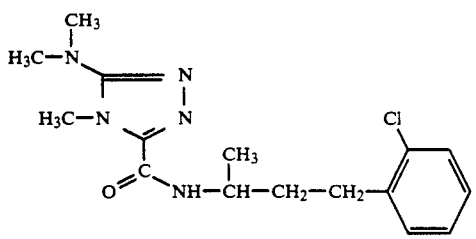

(Process a)

7.6 g (0.05 mol) of 1-amino2,2,3-trimethyl-guanidinium hydrochloride, 14.15 g (0.05 mol) of ethyl N-[1-(2-chlorophenyl)-3-butyl]oxamate and 5.4 g (0.1 mol) of sodium methylate are refluxed for 4 hours in 200 ml of ethanol, with stirring, the mixture is subsequently cooled to room temperature and filtered, the filtrate is concentrated in vacuo, the residue is taken up in dichloromethane, and the mixture is washed three times using 50 ml portions of water, dried over sodium sulphate and concentrated in vacuo. The residue is chromatographed over silica gel (eluent: cyclohexane/ethyl acetate 1:1). This gives 9.5 g (57% of theory) of N-[1-(2-chlorophenyl)-3-butyl]-5-dimethylamino-4-methyl-4H-1,2,4-triazol-3-ylcarboxamide as an oil.

$^1$H NMR (CDCl$_3$/tetramethylsilane): δ=1.82–1.90; 2.76–2.85; 2.90; 3.80 ppm.

PREPARATION OF THE STARTING COMPOUND

Example II-1

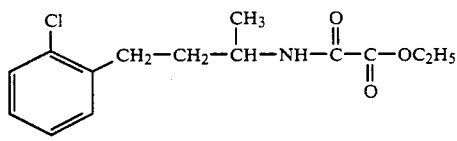

40.8 g (0.3 mol) of ethyl oxalyl chloride are added dropwise at room temperature with stirring and ice-cooling to 54.9 g (0.3 mol) of 1-(2-chlorophenyl)-3-butylamine (compare, for example, EP 6614) and 30.3 g (0.3 mol) of triethylamine in 400 ml of methylene chloride, and, when the addition has ended, the mixture is stirred for 30 minutes at room temperature, and triethylamine hydrochloride which has precipitated is subsequently filtered off. The filtrate is washed three times with 100 ml portions of water, dried over sodium sulphate and concentrated in vacuo.

This gives 82.2 g (97% of theory) of ethyl N-[1-(2-chlorophenyl)-3-butyl]oxamate as an oil.

$^1$H NMR (CDCl$_3$/tetramethylsilane): δ=1.25–1.28; 1.8–1.88; 4.02–4.12; 4.3–4.4; 7.1–7.25 ppm.

Example 2

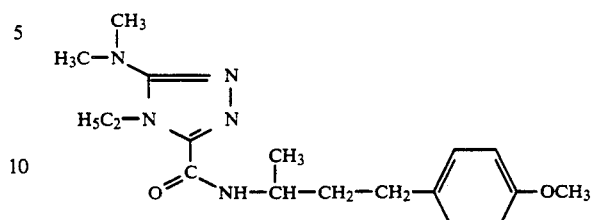

Process (a)

8.33 g (0.05 mol) of 1-amino-2,2-dimethyl-3-ethyl-guanidinium hydrochloride, 14.0 g (0.05 mol) of ethyl N-[1-(4-methoxyphenyl)-3-butyl]oxamate and 5.4 g (0.1 mol) of sodium-methylate are refluxed for 4 hours in 200 ml of ethanol, with stirring, the mixture is subsequently cooled to room temperature and filtered, the filtrate is concentrated in vacuo, the residue is taken up in dichloromethane, and the mixture is washed three times using 50 ml portions of water, dried over sodium sulphate and concentrated in vacuo. The residue is chromatographed over silica gel (eluent: cyclohexane/ethyl acetate 1:1).

This gives 10.4 g (60% of theory) of N-(1-(4-methoxy-phenyl)-3-butyl)-5-dimethylamino-4-ethyl-4H-1,2,4-triazol-3-ylcarboxamide of melting point m.p. 39°–40° C.

Preparation of the starting compound

Example II-2

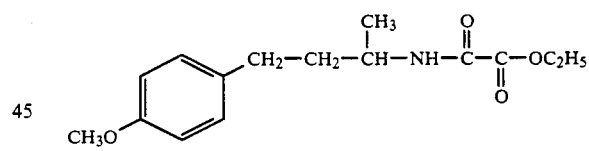

27.2 g (0.2 mol) of ethyl oxalyl chloride are added dropwise at room temperature with stirring and ice-cooling to 35.8 g (0.2 mol) of 1-(4-methoxyphenyl)-3-butylamine (compare, for example, EP 6614) and 20.2 g (0.3 mol) of triethylamine in 300 ml of methylene chloride, and, when the addition has ended, the mixture is stirred for 30 minutes at room temperature, and triethylamine hydrochloride which has precipitated is subsequently filtered off. The filtrate is washed three times using 100 ml portions of water, dried over sodium sulphate and concentrated in vacuo.

This gives 54.3 g (97% of theory) of ethyl N-[1-(4-methoxyphenyl)-3-butyl]oxamate as an oil.

$^1$H NMR (CDCl$_3$/tetramethylsilane): δ=1.21–1.23; 1.78–1.83; 3.88; 4.3–4.38; 7.05–7.10 ppm.

The following substituted triazoles of the general formula (I)

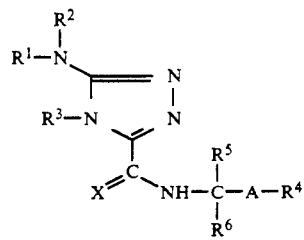

are obtained in a corresponding manner and following the general instructions for preparation:

| Example No. | −N(R¹)(R²) | R³ | R⁴ | R⁵ | R⁶ | A | X | physical properties |
|---|---|---|---|---|---|---|---|---|
| 3 | −N(CH₃)(CH₃) | CH₃ | 4-Cl-C₆H₄− | H | CH₃ | −CH(CH₃)−CH₂− | O | ¹H NMR*): 1.22–1.25; 1.9–2.0; 2.9; 3.8 |
| 4 | −N(CH₃)(CH₃) | CH₃ | 2-Cl-C₆H₄− | H | CH₃ | −CH₂−CH₂− | O | ¹H NMR*): 1.25–1.27; 2.3; 2.9; 3.8; 7.08; 7.32–7.32 |
| 5 | −N(CH₃)(CH₃) | CH₃ | 3,4-Cl₂-C₆H₃− | H | CH₃ | −CH₂−CH₂− | O | ¹H NMR*): 1.25–1.30; 2.6–2.7; 2.9; 3.8; 7.56–7.60 |
| 6 | −N(CH₃)(CH₃) | CH₃ | 4-F-C₆H₄− | H | CH₃ | −CH₂−CH₂− | O | ¹H NMR*): 1.25–1.28; 2.6–2.7; 2.9–3.8; 4.1–4.2 |
| 7 | −N(CH₃)(CH₃) | CH₃ | 3-CH₃-C₆H₄− | H | CH₃ | −CH(CH₃)−CH₂− | O | ¹H NMR*): 0.85–0.9; 1.23–1.27; 2.3; 2.9; 3.8 |
| 8 | −N(CH₃)(CH₃) | CH₃ | 2-CH₃-C₆H₄− | H | CH₃ | −CH(CH₃)−CH₂− | O | ¹H NMR*): 1.25–1.28; 1.9–2.05; 2.9; 3.8; 7.1; 7.25 |
| 9 | −N(CH₃)(CH₃) | CH₃ | C₆H₅− | H | CH₃ | −CH(CH₃)−CH₂− | O | ¹H NMR*): 0.85–0.9; 2.4–2.5; 2.9; 3.8 7.1–7.3 |
| 10 | −N(CH₃)(CH₃) | CH₃ | 4-OCH₃-C₆H₄− | H | CH₃ | −CH₂−CH₂− | O | ¹H NMR*): 1.25–1.27; 2.3–2.4; 2.9; 3.75; 3.8 |
| 11 | −N(CH₃)(CH₃) | CH₃ | 3-CF₃-C₆H₄− | H | CH₃ | −CH(CH₃)−CH₂− | O | ¹H NMR*): 0.85–0.9; 1.95–2.05; 2.9; 3.8; 7.3–7.45 |

-continued

| Example No. | -N(R¹)(R²) | R³ | R⁴ | R⁵ | R⁶ | A | X | physical properties |
|---|---|---|---|---|---|---|---|---|
| 12 | -N(CH₃)(CH₃) | CH₃ | 2,4-di(CH₃)-phenyl | H | CH₃ | -CH(CH₃)-CH₂- | O | ¹H NMR*): 0.85–0.9; 2.2; 2.9; 3.8; 7.8–7.85 |
| 13 | -N(CH₃)(CH₃) | CH₃ | 3-CF₃-phenyl | H | CH₃ | -CH₂-CH₂- | O | ¹H NMR*): 1.29–1.32; 1.85–1.95; 2.9; 3.8; 4.12–4.22 |
| 14 | -N(CH₃)(CH₃) | CH₃ | 4-OC₂H₅-phenyl | H | CH₃ | -CH₂-CH₂- | O | ¹H NMR*): 1.25–1.27; 1.38–1.42; 2.6–2.67; 2.9; 3.8 |
| 15 | -N(CH₃)(CH₃) | CH₃ | phenyl | H | H | -CH₂-N(C₂H₅)- | O | m.p.: 95–96° C. |
| 16 | -N(CH₃)(CH₃) | CH₃ | 4-iC₃H₇-phenyl | H | H | -CH(CH₃)-CH₂- | O | ¹H NMR*): 0.95–0.97; 1.22–1.25; 2.4–2.5; 2.9; 3.8 |
| 17 | -N(CH₃)(CH₃) | CH₃ | 4-OCH₃-phenyl | H | CH₃ | -CH₂-O- | O | ¹H NMR*): 1.4–1.43; 2.9; 3.75; 3.8; 3.95–4.03 |
| 18 | -N(CH₃)(CH₃) | CH₃ | 4-CH₃-phenyl | H | CH₃ | -CH₂-O- | O | ¹H NMR*): 1.4–1.43; 2,28; 2.9; 3.8; 3.95–4.05 |
| 19 | -N(CH₃)(CH₃) | CH₃ | 4-C₂H₅-phenyl | H | CH₃ | -CH₂-CH₂- | O | ¹H NMR*): 1.2–1.25; 1.26–1.29; 1.8–1.9; 2.9; 3.8 |
| 20 | -N(CH₃)(CH₃) | C₂H₅ | 4-iC₃H₇-phenyl | H | H | -CH(CH₃)-CH₂- | O | ¹H NMR*): 0.95–0.98; 1.2–1.25; 1.4–1.45; 2.9; 4.25–4.32 |
| 21 | -N(CH₃)(CH₃) | C₂H₅ | 3-CF₃-phenyl | H | CH₃ | -CH(CH₃)-CH₂- | O | ¹H NMR*): 1.25–1.28; 2.36–2.45; 2.9; 4.25–4.35 |
| 22 | -N(CH₃)(CH₃) | C₂H₅ | 3-CF₃-phenyl | H | CH₃ | -CH₂-CH₂- | O | ¹H NMR*): 1.28–1.32; 1.4–1.48; 2.7–2.8; 2.9 |
| 23 | -N(iC₃H₇)(CH₃) | CH₃ | 3-CF₃-phenyl | H | CH₃ | -CH₂-CH₂- | O | ¹H NMR*): 1.2–1.23; 1.26–1.3; 2.8; 3.75 |

-continued

| Example No. | -N(R¹)(R²) | R³ | R⁴ | R⁵ | R⁶ | A | X | physical properties |
|---|---|---|---|---|---|---|---|---|
| 24 | -N(iC₃H₇)(CH₃) | CH₃ | 4-OC₂H₅-phenyl | H | CH₃ | -CH₂-CH₂- | O | ¹H NMR*): 1.2-1.23; 1.38-1.43; 2.7; 3.75; 3.95-4.05 |
| 25 | -N(CH₃)(CH₃) | CH₃ | 4-Cl-phenyl | H | H | -CH(CH₃)-CH₂- | O | ¹H NMR*): 0.9-0.93; 2.9; 3.8; 7.55-7.6 |
| 26 | -N(CH₃)(CH₃) | CH₃ | phenyl | CN | CH₃ | -CH₂-CH₂- | O | ¹H NMR*): 1.85; 2.23-2.5; 2.9; 3.8; 7.18-7.32 |
| 27 | -N(CH₃)(CH₃) | CH₃ | 4-OCH₃-phenyl | CN | CH₃ | -CH₂-CH₂- | O | m.p.: 97-99° C. |
| 28 | -N(CH₃)(CH₃) | CH₃ | 4-Cl-phenyl | H | CH₃ | -CH₂-CH₂- | O | ¹H NMR*): 1.25-1.28; 2.62-2.7; 2.9; 3.8; 4.08-4.2 |
| 29 | -N(CH₃)(CH₃) | CH₃ | 2,5-diCl-phenyl | CH₃ | CH₃ | -CH₂-CH₂- | O | m.p.: 111-113° C. |
| 30 | -N(CH₃)(CH₃) | CH₃ | phenyl | CH₃ | CH₃ | -C≡C- | O | ¹H NMR*): 1.82; 2.9; 3.79 |
| 31 | -N(CH₃)(CH₃) | CH₃ | 4-Cl-phenyl | CH₃ | CH₃ | -CH₂-CH₂- | O | ¹H NMR*): 1.46; 2.9; 3.76 |
| 32 | -N(CH₃)(CH₃) | CH₃ | 4-F-phenyl | CH₃ | CH₃ | -CH₂-CH₂- | O | ¹H NMR*): 1.47; 2.9; 3.77 |
| 33 | -N(CH₃)(CH₃) | CH₃ | cyclohexyl (H) | H | iC₄H₉ | -CH₂-CH₂- | O | ¹H NMR*): 0.9-0.95; 1.15-1.7; 2.9; 3.8; 4.02-4.12; 7.03-7.08 |
| 34 | -N(CH₃)(CH₃) | CH₃ | 4-Cl-phenyl | CH₃ | CH₃ | -C≡C- | O | m.p. 181° C. |
| 35 | -N(CH₃)(CH₃) | CH₃ | 4-CH₃-phenyl | CH₃ | CH₃ | -CH₂-CH₂- | O | ¹H-NMR*): 1,47; 1,29; 2,89; 3,76 |

-continued

| Example No. | -N(R¹)(R²) | R³ | R⁴ | R⁵ | R⁶ | A | X | physical properties |
|---|---|---|---|---|---|---|---|---|
| 36 | -N(CH₃)(CH₃) | CH₃ | 4-C(CH₃)₃-C₆H₄- | CH₃ | CH₃ | -CH₂-CH₂- | O | ¹H-NMR*): 1,29; 1,47; 2,89; 3,77 |
| 37 | -N(CH₃)(CH₃) | CH₃ | 3-Cl-C₆H₄- | H | CH₃ | -CH₂-O- | O | ¹H-NMR*): 1,40–1,43; 2,9; 3,8; 4,0–4,03; 4,45–4,55 |
| 38 | -N(CH₃)(CH₃) | CH₃ | 4-(CH₂)₂-CH₃-C₆H₄- | H | CH₃ | -CH₂-CH₂- | O | ¹H-NMR*): 0,9–0,95; 1,25–1,3; 1,65–1,75; 2,5–2,55; 2,6–2,7; 3,03; 3,85; 4,1–4,2 |
| 39 | -N(CH₃)(CH₃) | CH₃ | 3,4-F₂-C₆H₃- | H | CH₃ | -CH₂-CH₂- | O | ¹H-NMR*): 1,17–1,2; 2,5–2,6; 2,85; 3,73 |

*)The ¹H NMR spectra were recorded in deuterochloroform (CDCl₃) or hexadeuterodimethyl sulphoxide (DMSO-d₆) using tetramethylsilane (TMS) as the internal standard. The chemical shift is given as the δ value in ppm.

Use Examples

In the following use example, the compound shown below was employed as the comparison substance

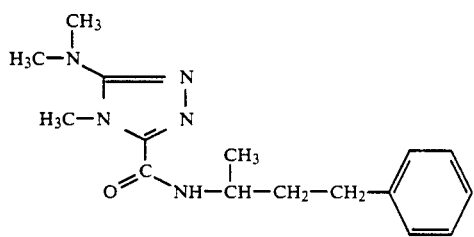

(A)

5-Dimethylamino-4-methyl-3-(4-phenylbut-2-ylaminocarbonyl)-1,2,4-triazole (disclosed in DE 3,809,053).

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area.

After three weeks, the degree of damage to the plants is rated in % damage in comparison to the development of the untreated control. The figures denote:

0% = no action (like untreated control)
100% = total destruction

A clearly superior activity and crop plant selectivity compared with the prior art is shown in this test, for example, by the compounds of the following Preparation Examples: 3, 4, 5, 6, 7, 9, 11, 12, 13, 14 and 19.

It will be understood that the specification and examples are illustrative but not limitative of the present invention and that other embodiments within the spirit and scope of the invention will suggest themselves to those skilled in the art.

What is claimed is:

1. A substituted triazole of the formula

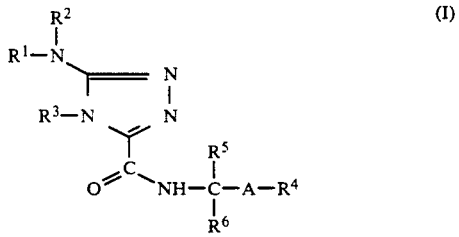

(I)

in which
R¹, R² and R³ each independently represents alkyl having 1 to 6 carbon atoms,
R⁴ represents phenyl, or phenyl substituted by halogen, trifluoromethyl or alkyl or alkoxy having 1 to 4 carbon atoms,
R⁵ and R⁶ each independently represents hydrogen or alkyl having 1 to 6 carbon atoms, and
A represents -CH₂-CH₂ or -CH(CH₃)-CH₂-,
but with the exception of the compound 5-dimethylamino-4-methyl-3-(4-phenylbut-2-ylaminocarbonyl)-1,2,4-triazole.

2. A substituted triazole according to claim 1, in which
R¹, R² and R³ each independently represents alkyl having 1 to 4 carbon atoms, $R^4$ represent phenyl, or phenyl substituted by halogen, trifluoromethyl or alkyl or alkoxy having 1 to 4 carbon atoms, $R^5$ and $R^6$ each independently represents hydrogen or alkyl having 1 to 4 carbon atoms.

3. A substituted triazole according to claim 1, in which $R^1$, $R^2$ and $R^3$ represent methyl, $R^4$ represents phenyl, or phenyl substituted by halogen, trifluoromethyl or alkyl or alkoxy having 1 or 2 carbon atoms, and $R^5$ and $R^6$ each independently represents hydrogen or methyl.

4. A compound according to claim 1, wherein such compound is

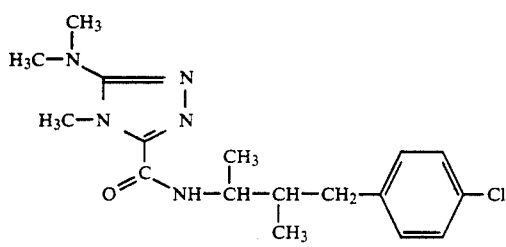

5. A compound according to claim 1, wherein such compound is

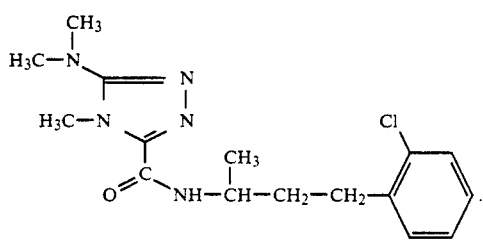

6. A compound according to claim 1, wherein such compound is

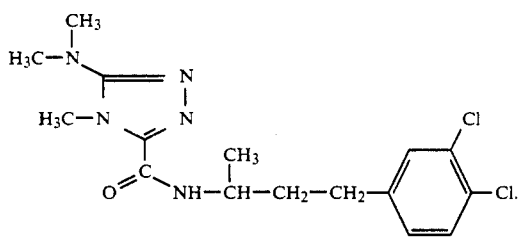

7. A compound according to claim 1, wherein such compound is

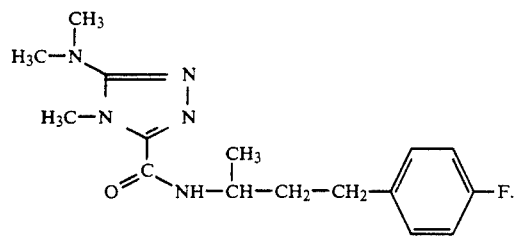

8. A compound according to claim 1, wherein such compound is

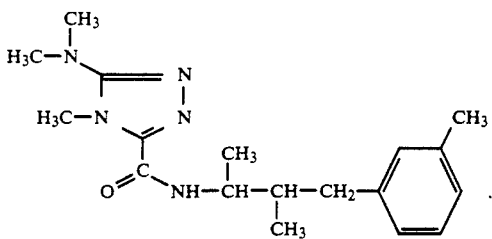

9. A compound according to claim 1, wherein such compound is

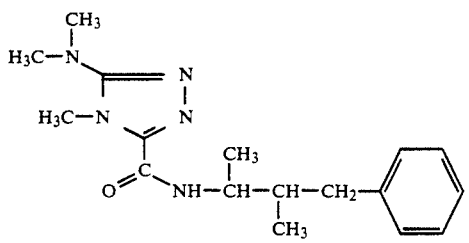

10. A compound according to claim 1, wherein such compound is

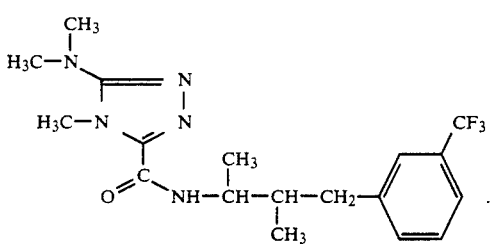

11. A compound according to claim 1, wherein such compound is

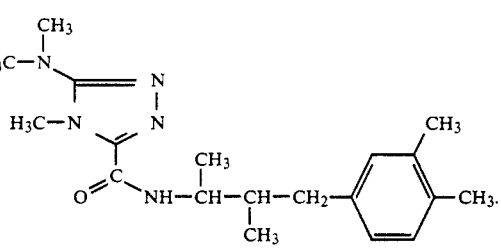

12. A compound according to claim 1, wherein such compound is

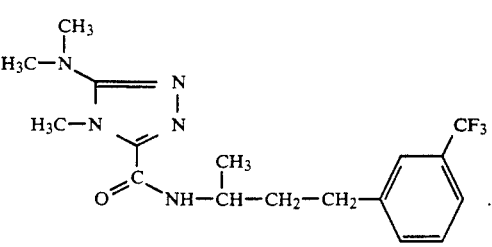

13. A compound according to claim 1, wherein such compound is

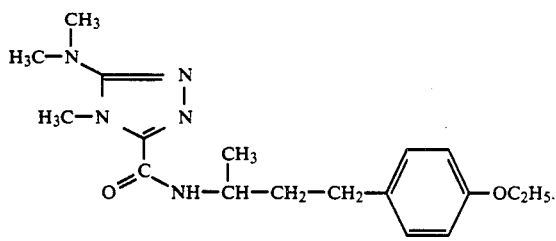

14. A compound according to claim 1, wherein such compound is

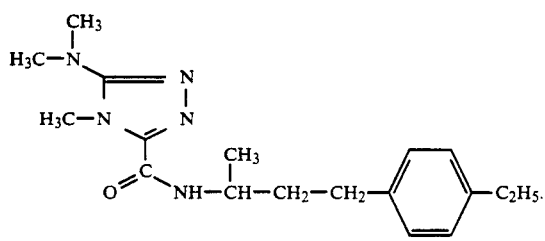

15. A compound according to claim 1, wherein such compound is

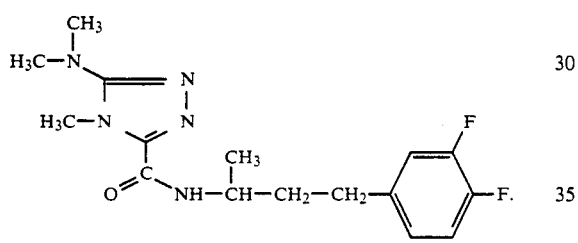

16. A herbicidal composition comprising a herbicidally effective amount of a compound according to claim 1 and a diluent.

17. A method of combating unwanted vegetation which comprises applying to such vegetation or to a locus from which it is desired to exclude such vegetation a herbicidally effective amount of a compound according to claim 1.

18. The method according to claim 17, wherein such compound is

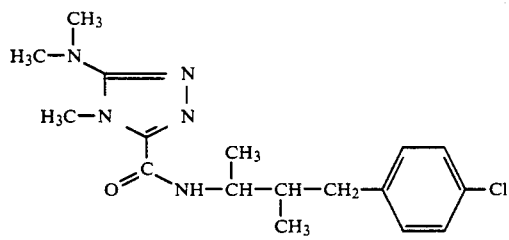

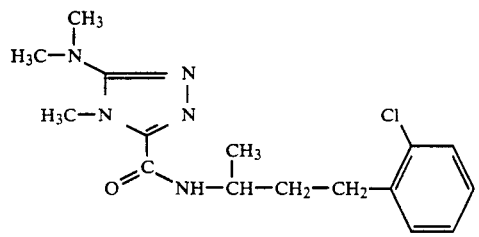

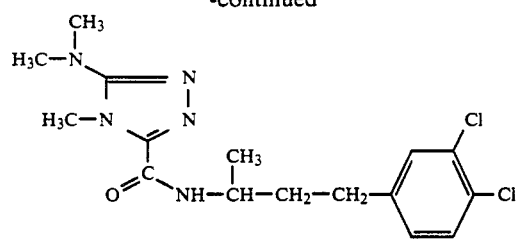

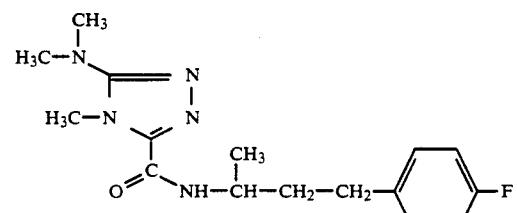

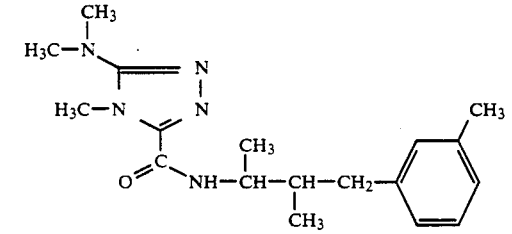

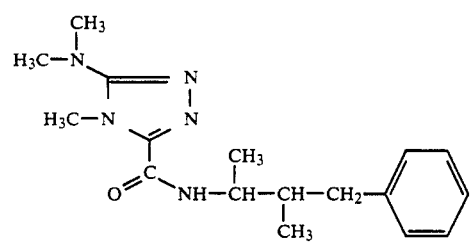

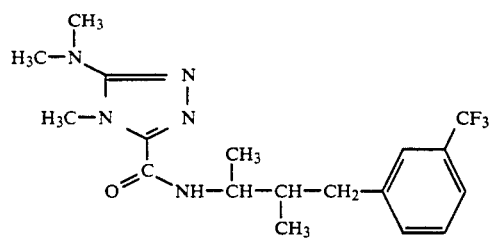

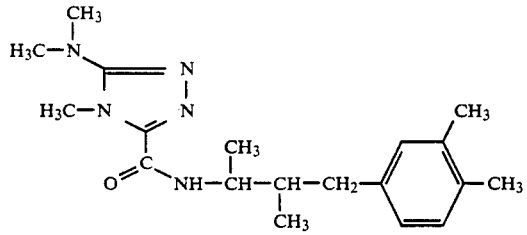

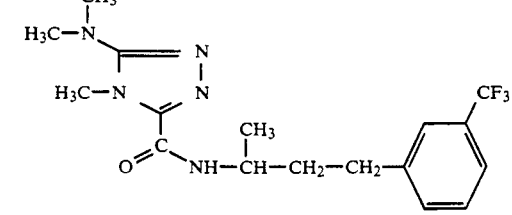

-continued
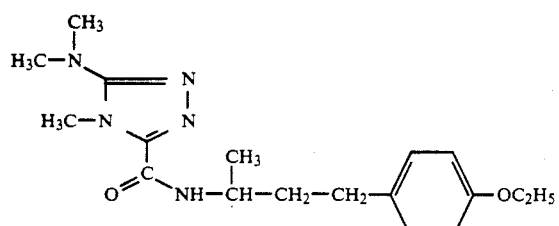
-continued
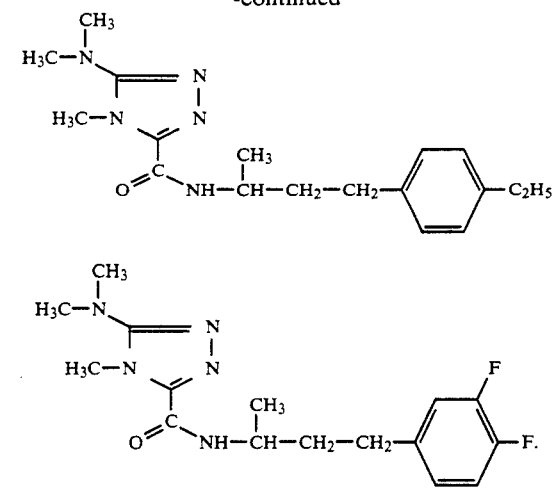
* * * * *